United States Patent [19]

Bruzzese et al.

[11] 4,372,961
[45] Feb. 8, 1983

[54] DERIVATIVES OF RIFAMYCINS, THEIR PREPARATION AND PHARMACEUTICAL COMPOSITIONS THEREOF

[76] Inventors: Tiberio Bruzzese, Via Frua 21/6, Milan, Italy, 20146; Lorenzo Ferrari, Via Biella 8, Milan, Italy, 20143

[21] Appl. No.: 284,565

[22] Filed: Jul. 17, 1981

[30] Foreign Application Priority Data

Jul. 18, 1980 [GB] United Kingdom ............... 8023606

[51] Int. Cl.³ ................ A61K 31/445; C07D 498/20
[52] U.S. Cl. ............................... 424/267; 260/239.3 P
[58] Field of Search ................. 260/239.3 P; 424/267

[56] References Cited
U.S. PATENT DOCUMENTS 3,829,417 8/1974 Maggi et al. ............... 260/239.3 P Primary Examiner—Robert T. Bond
Attorney, Agent, or Firm—Wenderoth, Lind & Ponack

[57] ABSTRACT

The present invention provides compounds of the general formula:

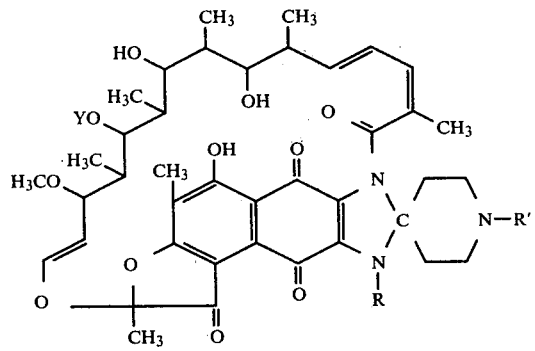

wherein Y is a hydrogen atom or an acetyl radical, R is a hydrogen atom, a straight-chained or branched, saturated or unsaturated aliphatic hydrocarbon radical containing up to 5 carbon atoms, which can be substituted by hydroxyl or amino groups, a phenyl radical which can be substituted by hydroxyl, amino or carboxyl groups or by alkoxycarbonyl radicals, an arylalkyl radical or a cycloalkyl radical containing 3 to 6 carbon atoms and R' is a hydrogen atom, a straight-chained or branched saturated or unsaturated aliphatic hydrocarbon radical containing up to 8 carbon atoms, which can be substituted by hydroxyl or amino groups, a cycloalkyl radical containing 3 to 6 carbon atoms or an arylalkyl radical; and the pharmacologically acceptable salts thereof. The present invention also provides a process for the preparation of these compounds, as well as pharmaceutical compositions containing them.

3 Claims, 3 Drawing Figures

DERIVATIVES OF RIFAMYCINS, THEIR PREPARATION AND PHARMACEUTICAL COMPOSITIONS THEREOF

BACKGROUND OF THE INVENTION

Several groups of rifamycin derivatives are known, all of which have quite similar structures.

From U.S. Pat. Nos. 4,124,585 and 4,124,586, it is known that 3-aminorifamycin SV can react with aldehydes to give Schiff's bases of 3-aminorifamycin SV itself or cyclic derivatives containing the following partial structure:

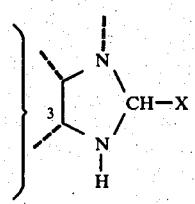

It was to have been expected that 3-aminorifamycin SV would also react with ketones but this is not so.

However, there is a need for new and improved derivatives of rifamycin and we have, surprisingly, found that 4-piperidinone derivatives react with 3-aminorifamycin S to give new compounds which have remarkable antibacterial properties.

SUMMARY OF THE INVENTION

Thus, according to the present invention there are provided new rifamycin derivatives of the general formula:

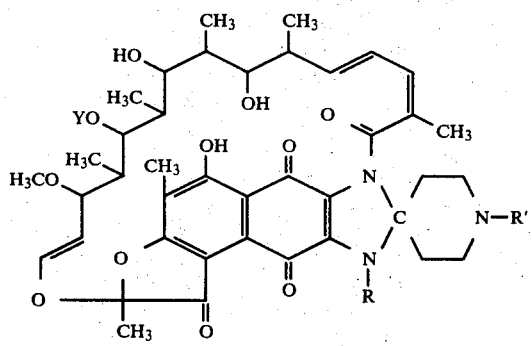

wherein Y is a hydrogen atom or an acetyl radical, R is a hydrogen atom, a straight-chained or branched, saturated or unsaturated aliphatic hydrocarbon radical containing up to 5 carbon atoms, which can be substituted by hydroxyl or amino groups, a phenyl radical, which can be substituted by hydroxyl, amino or carboxyl groups or by alkoxy carbonyl radicals, an arylalkyl radical or a cycloalkyl radical containing from 3 to 6 carbon atoms and R' is a hydrogen atom, a straight-chained or branched, saturated or unsaturated aliphatic hydrocarbon radical containing up to 8 carbon atoms, which can be substituted by hydroxyl or amino groups, a cycloalkyl radical containing from 3 to 6 carbon atoms or an arylalkyl radical; and the pharmacologically acceptable salts thereof.

DETAILED DESCRIPTION OF THE INVENTION

Figure 1:
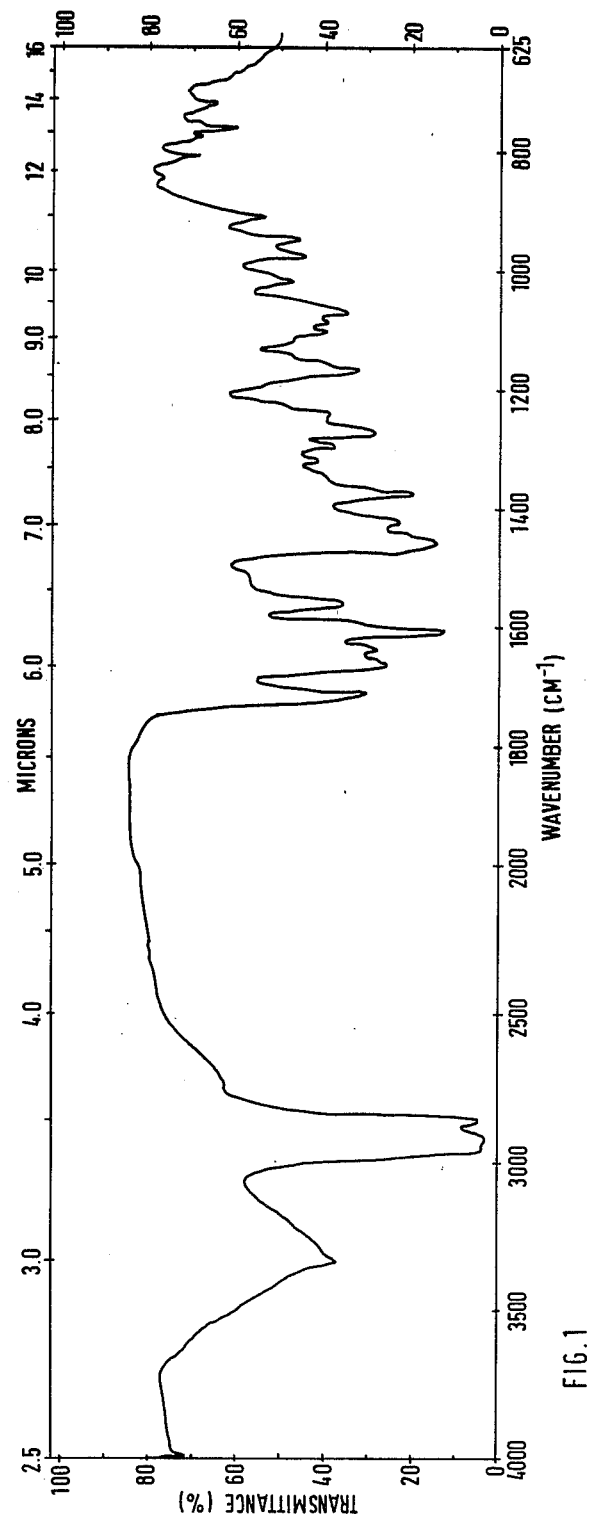

When R is an aliphatic hydrocarbon radical, it can be, for example, a methyl, ethyl, n-propyl, isopropyl, butyl or pentyl radical or an unsaturated analogue thereof and when it is a cycloalkyl radical it can be a cyclopropyl, cyclobutyl or cyclopentyl radical. When R' is an aliphatic hydrocarbon radical, it can be one of the preferred aliphatic hydrocarbon radicals mentioned above for R, as well as a hexyl, heptyl or octyl radical or an unsaturated analogue thereof, when it is a cycloalkyl radical it can be a cyclopropyl, cyclobutyl, cyclopentyl or cyclohexyl radical and when it is an aryalkyl it is preferably a benzyl radical.

These new compounds have a yellow colour and a light absorption maximum in methanolic solution at 400±5 nm. They dissolve in water at a pH of less than 6. Their ultraviolet absorption spectra in methanol have a characteristic pattern with maxima at 225 to 245 nm, at about 260 nm and at about 320 nm.

The new compounds can be prepared by reacting an optionally desacetylated 3-R-aminorifamycin S with a 4-piperidinone derivative of the general formula:

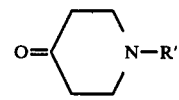

wherein R' has the same meaning as above. The reaction is preferably carried out in a solvent, for example methylene chloride, dioxan, methanol or tetrahydrofuran, preferably in the presence of an acidic catalyst, such as acetic acid, p-toluenesulphonic acid or the like.

Depending upon the reaction components used, the solvent used and the acid catalyst possibly used, the reaction takes place at different rates and may require the use of a temperature of from 0° C. to the boiling temperature of the solvent and a reaction time of from 1 to 2 hours to 48 to 96 hours. In general, the reaction is carried out at about ambient temperature for 12 to 48 hours to give a yield of 50 to 90% of a product of good purity.

In all cases, the course of the reaction can be monitored by thin layer chromatography on silica gel, using different solvent systems, for example chloroform:methanol (9:1 v/v) or benzene:methanol:ethyl acetate (60:21:24 v/v/v). The reaction is allowed to continue until the violet-brown spots of the 3-aminorifamycin reaction component has disappeared and until the characteristic yellow spot of the desired derivative of general formula (II) has formed completely.

The final product, which can be isolated by standard techniques, is often of high purity but, if necessary, it can be further purified by crystallisation from an appropriate solvent or, more generally, by column chromatography on silica gel, using, as eluent, a mixture of chloroform containing, by volume, 1 to 10% of methanol or 10 to 30% of acetone.

The new compounds of the present invention are soluble in many organic solvents, particularly in dimethylformamide and dimethyl sulphoxide; they are slightly soluble in water but, as already mentioned, they can be gradually dissolved by adding acids at a pH below 6 to give complete solutions which, for example, at pH 3 to 5, are very stable. On the other hand, a higher pH values, depending upon the nature of substituents R and R', the compounds (II) have a certain degree of instability which is still moderate around neutrality but is more marked at pH 9 to 10, gradually leading, due to hydrolysis and opening of the imidazole ring, to the corresponding 3-R-aminorifamycin S.

One of the most important characteristics of the new compounds of the present invention is their high antibiotic activity against gram-positive micro-organisms (*Staphylococcus aureus, Streptococcus faecalis, Streptococcus pyogenes, Diplococcus pneumoniae* and *Clostridium perfringens*), gram-negative micro-organisms (*Escherichia coli, Pseudomonas aeruginosa, Proteus vulgaris, Klebsiella pneumoniae* and *Salmonella tiphi*) and *Mycobacterium tuberculosis* H37 Rv.

Many of the new compounds (II) and particularly those in which R is a hydrogen atom or a methyl, ethyl, allyl or cyclopropyl radical, although being no more potent than the corresponding starting N-substituted 3-amino-rifamycins, are several times more active (MIC values on *Staphylococcus aureus* 1 to 4 ng/ml) than the known rifamycins used in therapy, such as rifampicin (MIC about 10 ng/ml).

On the other hand, even when quite voluminous substituents are present, for example, wherein R is an isopropyl, cyclohexyl, phenyl or benzyl radical, the compounds (II) maintain an activity similar to that of rifampicin, a real decrease in activity only being evidenced in a few cases, for example when R' is an octyl radical.

When the in vivo activity is determined, the new compounds of the present invention are found to be decidedly superior both to the 3-aminorifamycins and to rifampicin used as reference substance.

Pharmacokinetic tests carried out, for example on rats, clearly show, after oral administration, that the nature of the radicals R and R' has a marked influence on the absorption of the compounds, often leading to blood levels which are much higher than those obtained with the corresponding starting 3-aminorifamycins, for example of the order of 20 mcg/ml or more, when administered orally at 25 mg./kg. to rats, while the 3-aminorifamycins, administered in comparison tests, give blood levels of from an insignificant amount to about 1 to 2 mcg/ml. Several of the new compounds give prolonged and therapeutically useful blood levels even after 8 to 12 hours.

Furthermore, some of the new compounds according to the present invention display a high degree of tissue tropism in which low to medium blood levels are coupled with lung or liver levels which are 5 to 10 times higher. Consequently, the new compounds appear to be of great promise in the treatment of infections, such as tubercolosis, where tissue damage is prevalent.

The acute toxicity, tested in various animal species and by different routes of administration, gave markedly low results.

For the treatment of infections caused by gram-positive and gram-negative micro-organisms and especially of infections caused by *Mycobacterium tuberculosis*, the new compounds (II) of the present invention can be formulated for oral, topical and parenteral administration, the preferred route being, however, per os.

The formulations can be capsules, tablets or granulates or can be in the form of liquid preparations, such as syrups or elixirs. The liquid compositions may contain the active ingredient in suspension or solution, in effervescent or non-effervescent form, and may contain flavouring agents, suspending agents, colouring agents and the like.

The active ingredients may be diluted with appropriate solid or liquid excipients to give dosage units, each of which may contain, for example, from 25 to 500 mg. of active compound. Such dosage units may be administered one or more times a day, depending upon the specific activity of the compound, its bioavailability, the severity of the disease to be treated and the like. Formulations for topical use can be, for example, ointments, creams and lotions. For parenteral use, it is especially preferred to use the new compounds in a water-soluble form, for example as the hydrochlorides.

The following Examples are given for the purpose of illustrating the present invention:

EXAMPLE 1

10 g. 3-Aminorifamycin S are dissolved in 100 ml. methylene chloride and 4 ml. N-methyl-4-piperidinone and 2 ml. glacial acetic acid are added to the solution. The solution is then stirred for 5 hours at 20° C. and subsequently left overnight in a refrigerator. The yellow precipitate obtained is filtered off with suction, washed with cold methylene chloride and dried in a vacuum at 40° C. 8.5 g. of the desired product are obtained (II; $Y=COCH_3$; $R=H$; and $R'=CH_3$); assay (perchloric acid)=99.7%. The thin layer chromatogram (TLC) on silica gel 60 $F_{254}$ (Merck) shows a single spot with an Rf value of 0.47 (solvent system: chloroform/methanol 9:1 v/v). The infra-red absorption spectrum in a nujol mull exhibits maxima at characteristic wavelengths (see FIG. 1 of the accompanying drawing). The ultraviolet spectrum has absorption peaks in methanolic solution at 244, 260 and 324 nm.

EXAMPLE 2

Figure 2:
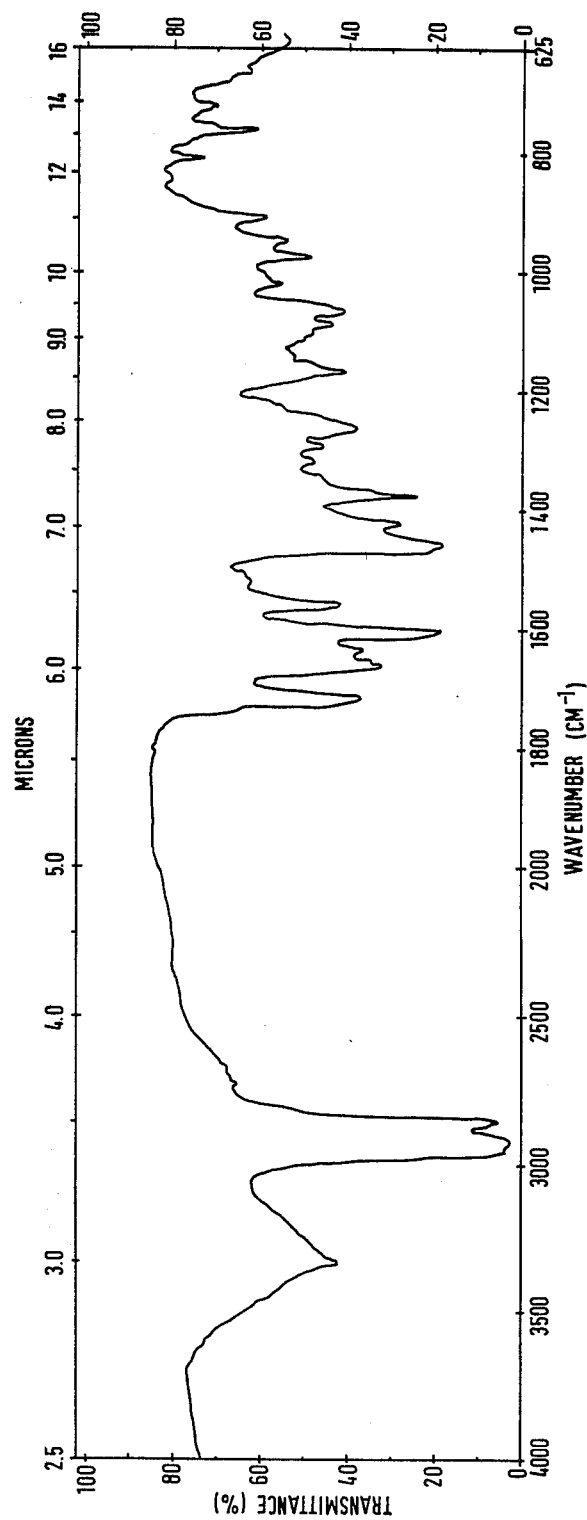

15 g. 3-Aminorifamycin S are dissolved in 120 ml. tetrahydrofuran and then 8 ml. N-n-butyl-4-piperidinone are added, followed by 6 ml. galcial acetic acid. The reaction mixture is stirred for 24 hours at ambient temperature and then diluted with 500 ml. diethyl ether and 500 ml. water. The aqueous phase is discarded and the organic phase is again washed with 500 ml. water. The ethereal solution is extracted with two 250 ml. portions of aqueous hydrochloric acid at pH 2.5. The combined acid extracts are washed with 200 ml. diethyl ether and then extracted with two 200 ml. portions of methylene chloride after having been buffered at pH 6 with disodium hydrogen phosphate. The methylene chloride extracts are washed with water, dried with anhydrous sodium sulphate and then concentrated under a vacuum to about 50 ml. The concentrate is diluted, while stirring, with 200 ml. diethyl ether and then stirred for a further 30 minutes. The yellow solid obtained is dried in a vacuum at 40° C. 7 g. of the desired product are obtained (II; $Y=COCH_3$; $R=H$; $R'=$n-butyl); assay (perchloric acid)=99%. TLC gives an Rf value of 0.65 under the conditions described in Example 1. The infra-red absorption spectrum is shown in FIG. 2 of the accompanying drawings.

EXAMPLE 3

Figure 3:
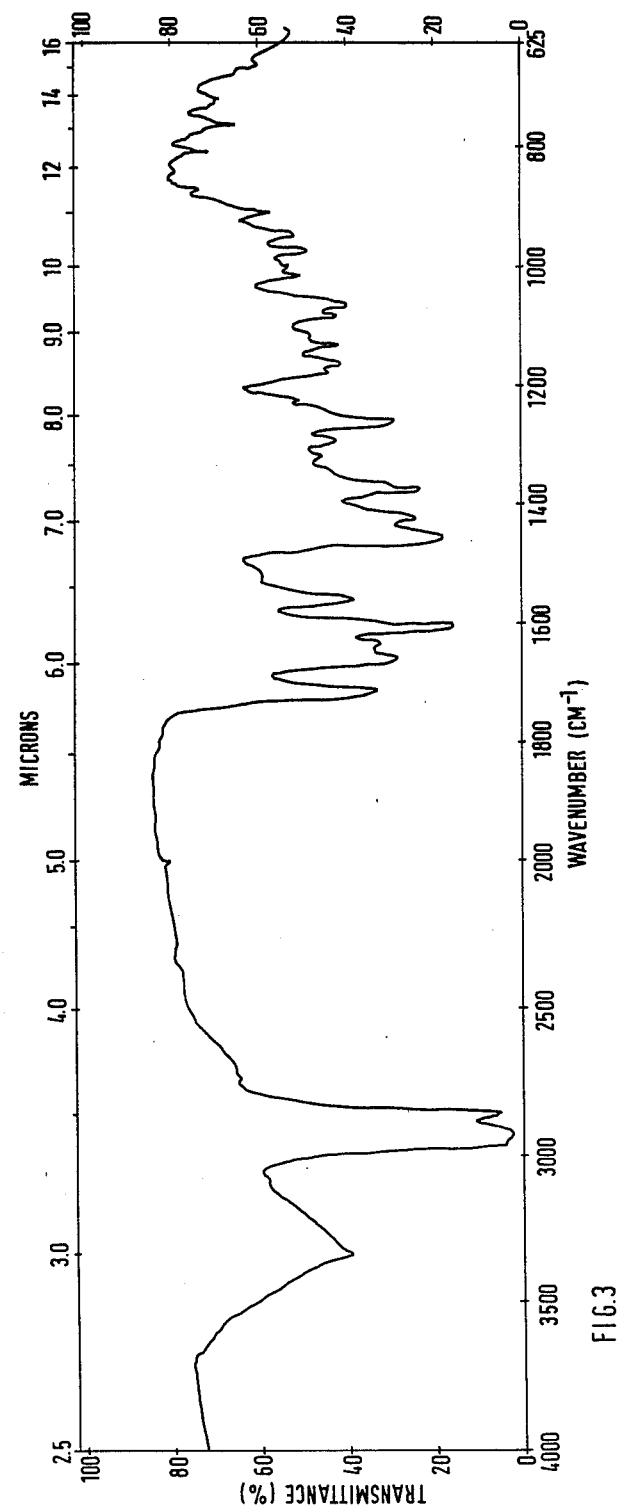

5 g. 3-Aminorifamycin S are dissolved in 50 ml. tetrahydrofuran. 3 g. N-Cyclopropyl-4-piperidinone are added, followed by 0.5 ml. glacial acetic acid. After 10 hours at 35° C., the reaction mixture is worked up as described in Example 2. 1.2 g. of the desired product are obtained (II; $Y=COCH_3$; $R=H$; $R'=$cyclopropyl);

assay (perchloric acid)=99.4%. The Rf value (TLC) under the usual conditions is 0.76 and the infra-red absorption spectrum is shown in FIG. 3 of the accompanying drawings.

EXAMPLE 4

10 g. 3-Aminorifamycin S (TLC: Rf=0.77 under the conditions described below) are dissolved in 100 ml. methylene chloride and then 7 ml. N-methyl-4-piperidinone and 3.5 ml. glacial acetic acid are added. The mixture is stirred for 12 hours at ambient temperature, a yellow precipitate gradually being obtained which is filtered off, well washed with diethyl ether and vacuum dried at 40° C. to give a 98% yield of a compound of general formula (II) (Y=COCH$_3$; R=H; R'=methyl); assay (perchloric acid)=99%; Rf by TLC on silica gel (60 F$_{254}$ Merck) (eluent benzene:methanol:ethyl acetate 60:21:24 v/v/v)=0.44.

EXAMPLE 5

By reacting 3-aminorifamycin S with the appropriate N-substituted 4-piperidinones in the manner described in Example 4, the following compounds of general formula (II) are obtained in which Y=COCH$_3$, R=H and R' has the meanings given in the following Table.

| R' | reaction time | yield | purity | Rf value |
|---|---|---|---|---|
| ethyl | 12 h. | 80% | 99% | 0.50 |
| allyl | 12 h. | 65% | 99.2% | 0.59 |
| butyl | 24 h. | — | 98.5% | 0.62 |
| i-butyl | 24 h. | — | 98% | 0.53 |
| octyl | 24 h. | 50% | 97.8% | 0.68 |
| cyclopropyl | 12 h. | — | 98.8% | 0.65 |
| cyclohexyl | 24 h. | 70% | 99% | 0.62 |
| benzyl | 24 h. | 74% | 98.5% | 0.72 |

EXAMPLE 6

6 g. 3-Methylaminorifamycin S are dissolved in 60 ml. methanol and then 4 ml. N-methyl-4-piperidinone and 0.1 g. p-toluenesulphonic acid are added. The reaction mixture is stirred at ambient temperature for 12 hours, a gradual change in colour from violet to yellow taking place. At the end of the reaction, the reaction mixture is evaporated to dryness and the residue is purified by column chromatography on silica gel, eluting first with chloroform:acetone (9:1 v/v) in order to eliminate any unreacted materials and minor impurities, and then with chloroform:acetone (7:3 v/v). The solution thus obtained is evaporated to dryness and the residue is washed with diethyl ether and then vacuum dried at 40° C. to give with a yield of 90% a compound of general formula (II) (Y=COCH$_3$; R=CH$_3$; R'=CH$_3$). The product has a purity of 99% (assay with perchloric acid) and has an Rf value by TLC on silica gel 60 F$_{254}$ (Merck) (eluent benzene:methanol:ethyl acetate 60:21:24 v/v/v) of 0.40.

EXAMPLE 7

The reaction of 3-methylaminorifamycin S with appropriately N-substituted 4-piperidinones in accordance with the procedure of Example 6 gives the following compounds of general formula (II), in which Y=COCH$_3$, R=CH$_3$ and R' has the meanings given in the following Table.

| R' | reaction time | yield | purity | Rf value |
|---|---|---|---|---|
| ethyl | 24 hr. | 90% | 98% | 0.49 |
| isopropyl | 24 hr. | 75% | 99% | 0.57 |
| allyl | 24 hr. | 80% | 98.5% | 0.59 |
| cyclopropyl | 48 hr. | — | 99.5% | 0.72 |
| cyclohexyl | 24 hr. | — | 99.2% | 0.61 |
| benzyl | 24 hr. | 77% | 98.2% | 0.70 |

EXAMPLE 8

By reacting 3-ethylaminorifamycin S with the appropriate 4-piperidinones according to the procedure of Example 6, the following compounds of general formula (II) are obtained in which Y=COCH$_3$, R=C$_2$H$_5$ and R' has the meanings given in the following Table.

| R' | reaction time | yield | purity | Rf value |
|---|---|---|---|---|
| methyl | 12 hrs. | 78% | 98% | 0.55 |
| ethyl | 24 hrs. | 88% | 99.5% | 0.61 |
| isopropyl | 48 hrs. | — | 98.2% | 0.65 |
| allyl | 24 hrs. | — | 98% | 0.67 |
| octyl | 72 hrs. | — | 97.5% | 0.76 |
| cyclopropyl | 48 hrs. | 80% | 99.8% | 0.70 |
| cyclohexyl | 24 hrs. | — | 99.5% | 0.72 |
| benzyl | 24 hrs. | 65% | 98% | 0.73 |

EXAMPLE 9

By reacting 3-cyclopropylaminorifamycin S with the appropriate N-substituted 4-piperidinones, generally following the procedure of Example 6, the following compounds of general formula (II) are obtained, in which Y=COCH$_3$, R=cyclopropyl and R' has the meanings given in the following Table.

| R' | reaction time | yield | purity | Rf value |
|---|---|---|---|---|
| methyl | 48 hrs. | 55% | — | 0.55 |
| ethyl | 48 hrs. | — | 99.7% | 0.55 |
| isopropyl | 48 hrs. | 60% | — | 0.61 |
| allyl | 48 hrs. | — | 99.5% | 0.64 |
| cyclopropyl | 72 hrs. | — | 98% | 0.69 |
| cyclohexyl | 48 hrs. | — | — | 0.63 |
| benzyl | 48 hrs. | 60% | 97.8% | 0.74 |

EXAMPLE 10

3-phenylaminorifamycin S is reacted with the appropriate N-substituted 4-piperidinones according to the procedure of Example 6, the following compounds of general formula (II) being obtained, in which Y=COCH$_3$, R=phenyl and R' has the meanings given in the following Table.

| R' | reaction time | yield | purity | Rf value |
|---|---|---|---|---|
| methyl | 24 hrs. | — | 99.2% | 0.63 |
| ethyl | 24 hrs. | 65% | — | 0.69 |
| isopropyl | 48 hrs. | 70% | 99% | 0.72 |
| allyl | 24 hrs. | — | — | 0.74 |
| cyclopropyl | 72 hrs. | — | — | 0.75 |
| cyclohexyl | 48 hrs. | 55% | 97.5% | 0.76 |
| benzyl | 48 hrs. | — | — | 0.80 |

EXAMPLE 11

By reacting appropriate N-substituted derivatives of 3-aminorifamycin S with appropriate 4-piperidinones according to the procedure described in Example 6, the following compounds of general formula (II) are obtained, in which Y=COCH$_3$ and R and R' have the meanings given in the following Table.

| R | R' | reaction time | yield | purity | Rf value |
|---|---|---|---|---|---|
| allyl | methyl | 24 hrs. | 80% | 98.6% | 0.64 |
| allyl | ethyl | 24 hrs. | 90% | 99% | 0.67 |
| allyl | allyl | 24 hrs. | 80% | 98.5% | 0.69 |
| allyl | benzyl | 48 hrs. | — | — | 0.80 |
| benzyl | methyl | 24 hrs. | — | 99% | 0.58 |
| benzyl | ethyl | 48 hrs. | — | — | 0.62 |
| benzyl | isopropyl | 48 hrs. | 65% | — | 0.69 |
| benzyl | benzyl | 72 hrs. | — | 97.5% | 0.80 |
| phenethyl | methyl | 24 hrs. | 70% | — | 0.65 |
| phenethyl | allyl | 24 hrs. | 80% | 99% | 0.86 |
| phenethyl | benzyl | 24 hrs. | — | — | 0.80 |

EXAMPLE 12

A solution of 3 g. 3-hydroxyethylaminorifamycin S in 30 ml. methanol is mixed with 2.3 ml. N-methyl-4-piperidinone, whereafter the reaction mixture is left to react for 48 hours at ambient temperature. The reaction mixture is then evaporated and the residue is purified by column chromatography on silica gel, eluting first with chloroform containing 1 to 2% by volume of methanol, discarding the eluate obtained, and then with chloroform containing 5 to 10% by volume of methanol to obtain the desired, pure reaction product. A product of general formula (II) is thereby obtained in 85–90% yield in which Y=acetyl, R=hydroxyethyl and R'=methyl. The compound has an assay of 99% (perchloric acid) and has an Rf value obtained by chromatography on silica gel 60 F$_{254}$ (Merck) (eluent benzene:methanol:ethyl acetate 60:21:24 v/v/v) of 0.35.

EXAMPLE 13

By reacting appropriate N-substituted derivatives of 3-aminorifamycin S with appropriate N-substituted 4-piperidinones according to the procedure of Example 12, there are obtained the following compounds of general formula (II), in which Y=COCH$_3$ and R and R' have the meanings given in the following Table:

| R | R' | reaction time | yield | purity | Rf value |
|---|---|---|---|---|---|
| hydroxyethyl | allyl | 48 hrs. | 80% | 98% | 0.50 |
| p-hydroxyphenyl | methyl | 24 hrs. | 75% | 98.5% | 0.52 |
| p-hydroxyphenyl | ethyl | 24 hrs. | 80% | — | 0.56 |
| p-hydroxyphenyl | cyclohexyl | 24 hrs. | 70% | — | 0.63 |
| p-carboxymethylphenyl | methyl | 24 hrs. | — | 99% | 0.10 |
| p-carboxymethylphenyl | cyclohexyl | 24 hrs. | — | — | 0.23 |

EXAMPLE 14

3 g. 25-Desacetyl-3-aminorifamycin S (TLC: Rf=0.71 under the conditions described below) are dissolved in 60 ml. methylene chloride, then 2 ml. N-methyl-4-piperidinone and 1 ml. glacial acetic acid are added and the reaction mixture is stirred for 72 hours at ambient temperature, whereafter the solvent is evaporated off and the residue is purified by column chromatography to give a high yield of a product of general formula (II) (Y=H, R=H, R'=CH$_3$). The compound has an assay of 98% (perchloric acid) and has an Rf obtained by TLC on silica gel 60 F$_{254}$ (Merck) (eluent benzene:methanol:ethyl acetate 60:21:24 v/v/v) of 0.43.

We claim:

1. A compound of the formula:

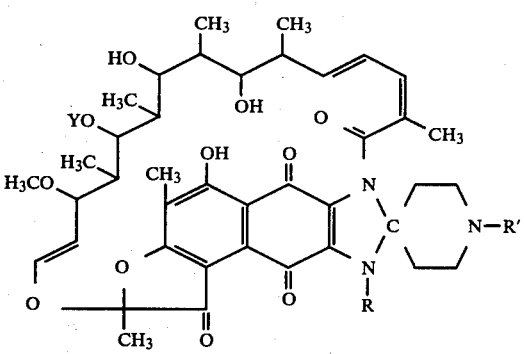

wherein Y is a hydrogen atom or an acetyl radical, R is a hydrogen atom, a straight-chained or branched, saturated or monoolefinically unsaturated aliphatic hydrocarbon radical, containing up to 5 carbon atoms, which can be substituted by hydroxyl or amino groups, a phenyl radical which can be substituted by hydroxyl, amino or by carboxyl groups, a benzyl or phenethyl radical or a cycloalkyl radical containing 3 to 6 carbon atoms and R' is a hydrogen atom, a straight-chained or branched saturated or monoolefinically unsaturated aliphatic hydrocarbon radical, containing up to 8 carbon atoms, which can be substituted by hydroxyl or by amino groups, a cycloalkyl radical containing 3 to 6 carbon atoms or a benzyl or phenethyl radical; and the pharmacologically acceptable salts thereof.

2. A process for the preparation of a compound of the formula:

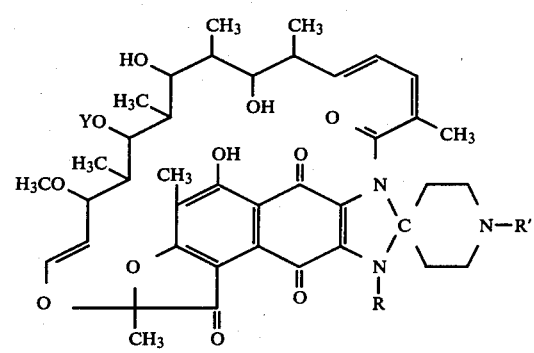

wherein Y is a hydrogen atom or an acetyl radical, R is a hydrogen atom, a straight-chained or branched, saturated or monoolefinically unsaturated aliphatic hydrocarbon radical, containing up to 5 carbon atoms, which can be substituted by hydroxyl or amino groups, a phenyl radical which can be substituted by hydroxyl, amino or by carboxyl groups, a benzyl or phenethyl radical or a cycloalkyl radical containing 3 to 6 carbon atoms and R' is a hydrogen atom, a straight-chained or branched saturated or monoolefinically unsaturated aliphatic hydrocarbon radical, containing up to 8 carbon atoms, which can be substituted by hydroxyl or by amino groups, a cycloalkyl radical containing 3 to 6 carbon atoms or a benzyl or phenethyl radical; and the pharmacologically acceptable salts thereof, which comprises reacting a 3-R-amino-rifamycin S in a solvent with a 4-piperidone derivative of the general formula:

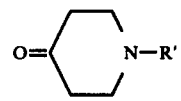

in which R' is as defined above.

3. Compositions with an antibiotic activity against gram-positive microorganisms comprising an antibiotically-effective amount of at least one compound of the general formula given in claim 1, in admixture with a solid or liquid pharmaceutical diluent or carrier.

* * * * *